(12) United States Patent
Olech

(10) Patent No.: US 7,022,214 B2
(45) Date of Patent: Apr. 4, 2006

(54) CARRIER AMPHOLYTES OF HIGH PH RANGE

(75) Inventor: Lee Olech, Rodeo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 260 days.

(21) Appl. No.: 10/763,405

(22) Filed: Jan. 21, 2004

(65) Prior Publication Data
US 2005/0155862 A1 Jul. 21, 2005

(51) Int. Cl.
*G01N 27/26* (2006.01)
*C07C 279/00* (2006.01)
*C07C 279/12* (2006.01)

(52) U.S. Cl. .......... 204/459; 204/548; 204/610; 204/644; 564/248; 564/511; 564/512; 525/54.1; 525/54.11; 525/420; 525/421; 528/229; 528/324; 528/332; 528/339.5

(58) Field of Classification Search ........ 204/450–470, 204/600–621; 564/248, 511–512; 525/54.1–54.11, 525/420–421; 528/229, 324, 332, 339.5; 514/634–635
See application file for complete search history.

(56) References Cited

U.S. PATENT DOCUMENTS

| | | | |
|---|---|---|---|
| 3,499,927 A * | 3/1970 | Badcock et al. | ............ 564/236 |
| 3,770,603 A | 11/1973 | Grubhofer et al. | |
| 4,131,534 A | 12/1978 | Just | |
| 5,173,160 A | 12/1992 | Rodkey et al. | |
| 5,319,046 A | 6/1994 | Kozulic et al. | |
| 5,322,906 A | 6/1994 | Rodkey et al. | |
| 5,428,116 A | 6/1995 | Rodkey et al. | |
| 5,432,202 A * | 7/1995 | Cherksey et al. | ........... 514/626 |
| 6,380,358 B1 | 4/2002 | Goodman et al. | |

FOREIGN PATENT DOCUMENTS

| | | |
|---|---|---|
| DE | 2137617 C3 | 1/1979 |
| DE | 2230743 B2 | 8/1980 |
| GB | 1402751 | 8/1975 |
| GB | 1435744 | 5/1976 |
| WO | WO 88/09981 A2 | 6/1988 |

OTHER PUBLICATIONS

"2-Dimensional Electrophoresis—Separation: First Dimension IEF"; Amersham Biosciences; http://www1.amershambiosciences.com/aptrix/upp00919.nsf/Content/Elpho_2D_1st_Dim., Sep. 2003.

"One Dimensional Protein Electrophoresis Seperation: Isoelectric focusing of proteins"; http://www4.amershambiosciences.com/aptrix/upp00919.nsf/Content/Elpho_IEF+Seperation, Sep. 2003.

"NCT Proteomics Group: Methods"; http://dir.niehs.nih.gov/proteomics/methods.htm., Sep. 2003.

* cited by examiner

*Primary Examiner*—Nam Nguyen
*Assistant Examiner*—Jeffrey Barton
(74) *Attorney, Agent, or Firm*—M. Henry Heines; Townsend and Townsend and Crew, LLP

(57) ABSTRACT

Carboxylic acid-substituted polyalkylene polyamines in which amine nitrogen atoms on the polyamine backbone structure are replaced by guanidine groups provide a pH range extending into high pH values. These substances are useful as carrier ampholytes in isoelectric focusing.

19 Claims, 1 Drawing Sheet

CARRIER AMPHOLYTES OF HIGH PH RANGE

BACKGROUND OF THE INVENTION

1. Field of the Invention

This invention resides in the field of protein separations in biochemical research, and in particular the chemical species and mixtures used as carrier ampholytes in isoelectric focusing.

2. Description of the Prior Art

Of the two principal classes of-resolving media used in isoelectric focusing, carrier ampholytes offer certain advantages over immobilized pH gradients. One advantage is a particularly wide range of isoelectric point variation among individual species of an ampholyte mixture. Another is the versatility that arises from the ability of the ampholytes to function either in the liquid phase or on a solid or semi-solid support medium such as polyacrylamide, agarose, and Sephadex. This versatility permits separations to be performed on a large scale as well as a small scale, making it convenient both for preparative separations and for use in the research laboratory.

The pH range of any particular ampholyte mixture determines the type of separation that can be performed and the degree of resolution among solutes in the sample mixture. While the typical carrier ampholyte mixture of the prior art offers a pH range that extends well into the acid and base ranges, the typical upper end of the range is about 10.0. The effectiveness of ampholytes towards the outer reaches of the range is also limited by the tendency of ampholyte pH gradients to shift over time. This shift of the gradient often causes the gradient to flatten at each end, particularly at the upper end above pH 9. This limits the mixtures that can be separated effectively, and is particularly detrimental to two-dimensional electrophoresis in this range when isoelectric focusing in carrier ampholytes is used as the first dimension.

SUMMARY OF THE INVENTION

This invention resides in novel classes of carrier ampholytes that are capable of being synthesized to have high isoelectric points, including values above 10.0, and in many cases above 12.0. While the most typical carrier ampholytes of the prior art are formed from polyalkylene polyamines in which varying proportions of the nitrogen atoms have been substituted with carboxyethyl groups, the ampholytes of the present invention differ, at least in part, by the inclusion of guanidine groups in the polyalkylene polyamine backbone.

A generic formula for the carrier ampholytes of the present invention is as follows:

$$X\text{-}((CH_2)_m\text{—}Y)_n\text{-}(CH_2)_m\text{-}Z \qquad (I)$$

in which m and n are integers and X, Y, and Z represent basic groups that are combinations of amine groups and guanidine groups, substituted with carboxyalkyl groups to varying degrees. The total number of possible combinations depends on the length of the chain in a particular structure as determined by the value of n and hence total number of X, Y, and Z groups. Thus, in cases where n is greater than one, resulting in two or more Y groups on a single molecule, the Y groups may vary among each other. Ampholyte mixtures in accordance with this invention will therefore include multiple species of Formula I varying in the number of carboxyalkyl groups bonded to the structure at its nitrogen atoms, and in some cases both the number of carboxyalkyl groups and the number of amine groups that have been replaced with guanidine groups.

This invention thus resides in carrier ampholytes above the above formula, mixtures of ampholytes of the above formula with isoelectric points varying among the ampholytes of each mixture, and combinations of isolated ampholytes or of isolated ampholyte fractions of the above formula in which each ampholyte or fraction has a characteristic isoelectric point or range distinguishing that ampholyte or fraction from the others in the combination. Still further, this invention resides in a method for separating components of a sample, and particularly components of high isoelectric points, by isoelectric focusing in a pH gradient established by an array of carrier ampholytes of the above formula.

These and other features, aspects, objections and advantages of the invention will be apparent from the description that follows.

BRIEF DESCRIPTION OF THE FIGURE

The attached FIGURE is a reaction scheme for the preparation of a certain carrier ampholytes within the scope of the present invention.

DETAILED DESCRIPTION OF THE INVENTION AND PREFERRED EMBODIMENTS

Figure 1:
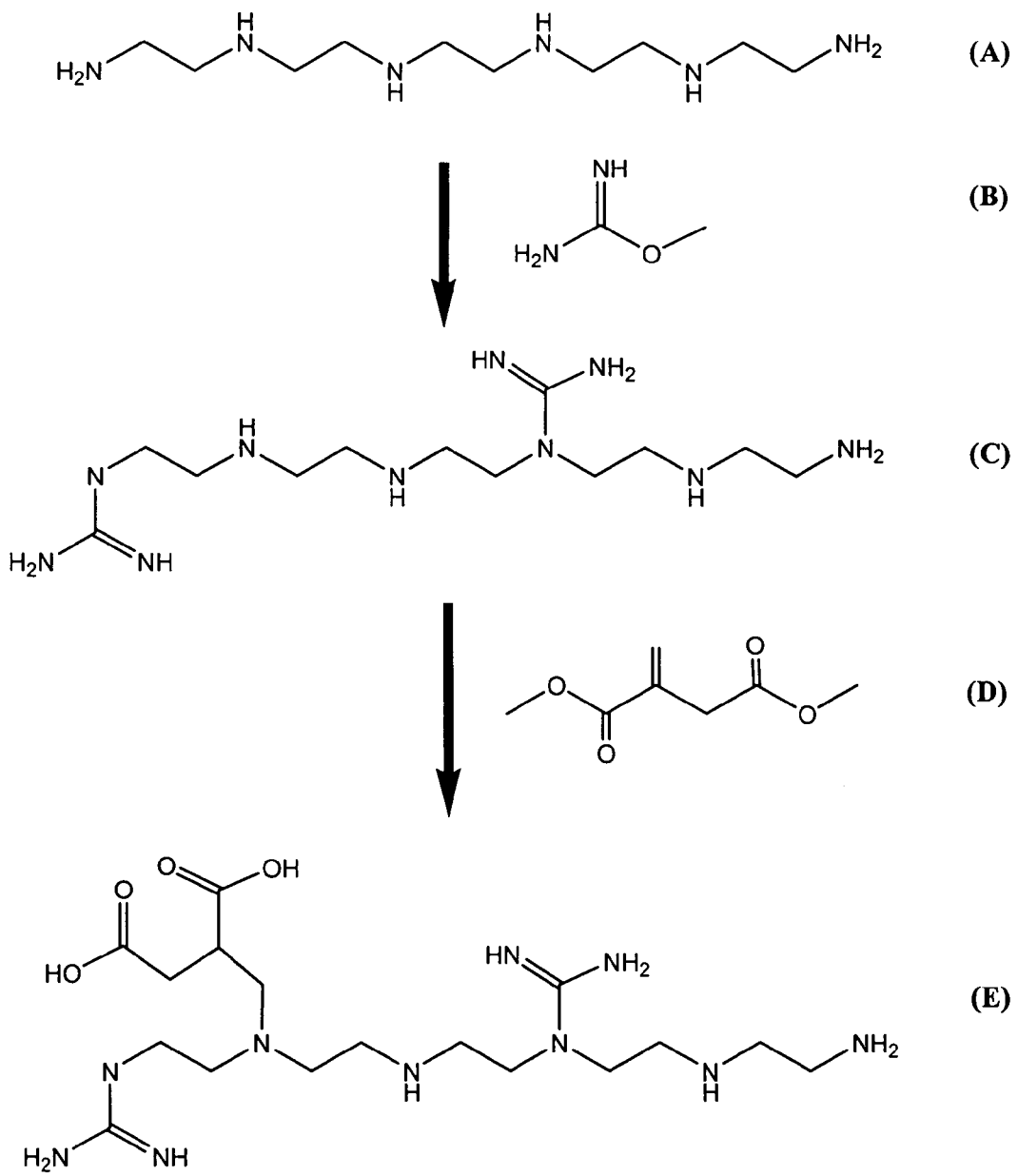

In Formula I above, m is 1 to 6, n is 1 to 20, and when n is 2 or greater, the invention extends to structures in which the two or more Y groups are the same as well as those in which the Y groups are not all the same, i.e., one or more may differ from the others. A preferred range of m is 1 to 3, and a particularly preferred value is 2, in which case the group bridging the nitrogen atoms on the backbone of the structure is the ethylene group ($—CH_2CH_2—$). A preferred range for n is 1 to 10, a more preferred range is 1 to 6, and in particularly preferred embodiments, n is 4. Since, as will be explained below, the starting materials for the synthesis of ampholytes are the polyalkylene polyamines, examples of polyalkylene polyamines from which ampholytes of the above description can be prepared are diethylenetriamine (DETA), triethylenetetramine (TETA), tetraethylenepentamine (TEPA), and pentaethylenehexamine (PEHA).

Each of X, Y, and Z is either an amine group or a guanidine group such that the structure contains a combination of amine and guanidine groups, i.e., at least one group at the X, Y, or Z locations, but not all, is a guanidine group and the rest are amine groups. The groups covalently bonded to the amine N atoms are either H or alkyl groups, and preferred amine groups are fully alkyl-substituted, and the alkyl groups other than those joining adjacent N atoms are preferably $C_{1-4}$ alkyl groups, more preferably methyl or ethyl, and most preferably methyl groups.

At last one amine group in the polyamine backbone of the structure of Formula I is substituted with at least one carboxylate substituent having the formula

(II)

in which $R^1$ is either H, $C_{1-4}$ alkyl, $C(O)OH$, $C(O)O—(C_{1-4}$ alkyl), $(C_{1-4}$ alkylene)-$C(O)OH$, or $(C_{1-4}$ alkylene)-$C(O)O—(C_{1-4}$ alkyl); $R^2$ is either H, $C_{1-4}$ alkyl, $C(O)OH$, $C(O)O—(C_{1-4}$ alkyl), $(C_{1-4}$ alkylene)-$C(O)OH$, or $(C_{1-4}$ alkylene)-$C(O)O—(C_{1-4}$ alkyl); and $R^3$ is either H or $C_{1-4}$ alkyl.

Since, as will be explained below, the carboxylate substituents of Formula II are bonded to the backbone by the reaction of the unsubstituted backbone with an α,β-unsaturated carboxylic acid, examples of such acids that will result in compounds with these substituents are acrylic acid, methacrylic acid, methylene malonic acid, ethylene malonic acid, crotonic acid, maleic acid, fumaric acid, and itaconic acid. Combinations of these acids can also be used, to result in ampholyte molecules with two or more different carboxylate substituents or an ampholyte mixture with different carboxylate substituents on different components of the mixture.

The ampholytes of this invention are synthesized by conventional methods. Examples of guanidinylation agents are cyanamides, O-alkyl isoureas, aminoiminosulfonic acid, aminoiminoethane sulfonic acid, 1H-pyrazole-1-carboxamidine hydrochloride, N,N'-bis(tert-butoxycarbonyl)-S-methylthiourea, and alkanesulfonyl guanidines. An example of a disclosure of guanidinylation reagents in the literature is Goodman, et al., U.S. Pat. No. 6,380,358 (Apr. 30, 2002), incorporated herein by reference.

Addition of the carboxylic acid to the guanidine-containing backbones is likewise achieved by conventional methods known in the art. Such methods are disclosed, for example, in Rodkey et al., U.S. Pat. No. 5,173,160 (Dec. 22, 1992), incorporated herein by reference. Prominent among these methods is the reaction of the unsubstituted backbone compound with an α,β-unsaturated carboxylic acid as described above.

An illustration of a reaction scheme for the preparation of the guanidine-containing ampholytes of the present invention appears in FIG. 1. The starting material is pentaethylene hexamine (PEHA) (A). Guanidinylation in achieved by reaction with O-methyl isourea (B) to form a mixture of intermediates, of which one representative species (C) is shown. In this species, two of the amine N atoms on the PEHA structure have been converted to guanidine groups. Other species in the mixture will differ in the number of N atoms converted to guanidine groups and the location of the N atoms on the starting PEHA structure. The intermediates mixture is reacted with dimethyl itaconate (D) to achieve a final ampholyte mixture of which one species (E) is shown. In this species, a succinylmethyl group has become covalently bonded to only one of the N atoms that had not been converted to a guanidine group, while other species of the mixture may contain two or more succinylmethyl groups in addition to differences in the number and location of guanidine groups.

Ampholyte mixtures in accordance with this invention can be separated into isoelectric point fractions, and can likewise aid in the separation of sample mixtures into isoelectric point solute fractions, by conventional isoelectric focusing methods. These methods include the use of gels, liquids, beads, or other media, by loading the medium with the mixtures to be separated and establishing a pH gradient with an electric potential across the medium until solute migration ceases. Sample mixtures that can be separated in this manner include enzymes, hormones, antibodies, antibody fragments, polypeptides and proteins in general, as well as nucleic acids and other macromolecules and small molecules. The separation of sample mixtures can be achieved by first distributing the ampholytes in the suspending medium at locations corresponding to their pH, or most conveniently by first combining the ampholyte mixture and the sample mixture, placing the combined mixture in the suspending medium, and finally establishing the pH gradient with an electric potential across the medium. In accordance with prior art methods of isoelectric focusing, both continuous and discontinuous media can be used. Continuous media include gels, liquids, and granules, either in columns, tubes, slab-shaped configurations, or capillaries, and discontinuous media include segmented isoelectric focusing apparatus with a different ampholyte fraction in each segment. The ampholyte fractions circulate through the apparatus in independent circuits while the sample solutes are free to migrate between the various segments until equilibrium is reached due to the arrival of a solute at a segment whose pH equals the isoelectric point of the solute. Descriptions of apparatus of this type are found in Bier, U.S. Pat. No. 4,204,929 (May 27, 1980), Bier, U.S. Pat. No. 4,362,612 (Dec. 7, 1982), and Bier, U.S. Pat. No. 4,588,492 (May 13, 1986), the contents of each of which are incorporated herein by reference. Examples of commercially available apparatus are the ROTOFOR® and MINI ROTOFOR® Cells of Bio-Rad Laboratories, Inc.

The following example is presently for purposes of illustration and is not intended to limit the scope of this invention.

EXAMPLE

This example illustrates the synthesis of a carrier ampholyte by the guanidination of pentaethylene hexamine followed by the addition of carboxylic acid groups by reaction with dimethyl itaconate.

Pentaethylene hexamine (PEHA) (18.8 g or 0.48 mole of amino groups) was mixed with water to a total of 90 g. To this solution was added 20 g (0.8 mole) of O-methyl isourea, and the mixture was heated to 60° C. in 5 minutes and maintained at that temperature for 5 minutes more. The pH of the resulting solution was 10.77. This material was passed through an anion exchange column containing approximately 600 mL of a 20–50 mesh polystyrene-divinylbenzene quaternary ammonium anion exchange resin in hydroxide form (AG 1-X8 of Bio-Rad Laboratories, Inc., Hercules, Calif., USA) to remove sulfate ions. The pH of the collected material was 13.5.

A round-bottom flask was charged with 100 mL of this product and heated to 40° C., and dimethyl itaconate (15.6 g) was added, causing the temperature to spontaneously rise to 47° C. The temperature was then adjusted to 50° C. and the reaction continued at that temperature for 22 hours. The temperature was then raised to 60° C. and maintained at that level for approximately 90 hours.

Product (112 mL) was collected and had a pH of 8.66. This was passed through a column of Bio-Rad AG 4-X4 tertiary amine resin in free base form to remove acid groups not bound to the polyamino compounds. The pH of the collected effluent was 9.1.

The effluent was fractionated on a twenty-chamber ROTOFOR® Cell (Bio-Rad Laboratories, Inc.) to yield fractions of the following pH values:

| Reaction Product of Guanidinated PEHA and Dimethyl Itaconate: Ampholyte Fractions | |
|---|---|
| Fraction No. | pH |
| 20 | 1.35 |
| 19 | 1.83 |
| 18 | 2.77 |
| 17 | 3.32 |
| 16 | 3.81 |

-continued

Reaction Product of Guanidinated PEHA and Dimethyl Itaconate: Ampholyte Fractions

| Fraction No. | pH |
| --- | --- |
| 15 | 4.42 |
| 14 | 5.16 |
| 13 | 7.16 |
| 12 | 8.07 |
| 11 | 9.28 |
| 10 | 10.31 |
| 9 | 12.24 |
| 8 | 12.70 |
| 7 | 12.96 |
| 6 | 13.07 |
| 5 | 13.19 |
| 4 | 13.26 |
| 3 | 13.31 |
| 2 | 13.34 |
| 1 | 13.36 |

The foregoing description is offered primarily for purposes of illustration. Further modifications, substitutions and variations will be apparent to those skilled in the art and will be included within the scope of the invention.

What is claimed is:

1. A compound having the formula

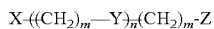

in which:
m is 1 to 6;
n is 1 to 20;
when n is 2 or greater, either all Y is the same or Y differs among different (—(CH$_2$)$_m$—Y—) groups; and
X, Y, and Z are independently selected from the group consisting of amine groups and guanidine groups such that at least one group represented by X, Y, and Z, but not all, is a guanidine group; and
at least one amine group represented by X, Y, or Z is substituted with at least one carboxylate substituent having the formula

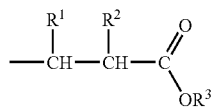

in which:
$R^1$ is a member selected from the group consisting of H, $C_{1-4}$ alkyl, C(O)OH, C(O)O—($C_{1-4}$ alkyl), ($C_{1-4}$ alkylene)-C(O)OH, and ($C_{1-4}$ alkylene)-C(O)O—($C_{1-4}$ alkyl);
$R^2$ is a member selected from the group consisting of H, $C_{1-4}$ alkyl, C(O)OH, C(O)O—($C_{1-4}$ alkyl), ($C_{1-4}$ alkylene)-C(O)OH, and ($C_{1-4}$ alkylene)-C(O)O—($C_{1-4}$ alkyl); and
$R^3$ is a member selected from the group consisting of H and $C_{1-4}$ alkyl.

2. The compound of claim 1 wherein:
$R^1$ is a member selected from the group consisting of H, CH$_3$, C(O)OH, C(O)OCH$_3$, CH$_2$C(O)OH, and CH$_2$C(O)OCH$_3$;
$R^2$ is a member selected from the group consisting of H, CH$_3$, C(O)OH, C(O)OCH$_3$, CH$_2$C(O)OH, and CH$_2$C(O)OCH$_3$; and
$R^3$ is a member selected from the group consisting of H and CH$_3$.

3. The compound of claim 1 wherein m is 1 to 3.

4. The compound of claim 1 wherein m is 2 and n is 1 to 10.

5. The compound of claim 1 wherein m is 2 and n is 1 to 6.

6. The compound of claim 1 wherein m is 2 and n is 4.

7. A composition of matter comprising a plurality of compounds of claim 1 differing in the number of said carboxylate substituents per molecule.

8. A composition of matter comprising a plurality of compounds of claim 1 differing in the number of guanidine groups per molecule.

9. A kit for performing isoelectric focusing, comprising a plurality of compounds of claim 1 having isoelectric points ranging from about 3.0 to about 13.0.

10. A kit for performing isoelectric focusing, comprising a plurality of compounds of claim 1 having isoelectric points ranging from about 8.0 to about 13.0.

11. A kit for performing isoelectric focusing, comprising a plurality of compounds of claim 1 having isoelectric points ranging from about 9.0 to about 12.0.

12. In a method for separating components of a sample according to isoelectric point, said method comprising imposing an electric potential across an electrophoresis medium loaded with said sample, said electrophoresis medium having suspended therein a plurality of carrier ampholytes distributed throughout said medium according to isoelectric point to form a pH gradient therein, the improvement in which said carrier ampholytes are compounds having the formula

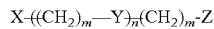

in which:
m is 1 to 6;
n is 1 to 20;
when n is 2 or greater, either all Y is the same or Y differs among different (—(CH$_2$)$_m$—Y—) groups; and
X, Y, and Z are independently selected from the group consisting of amine groups and guanidine groups such that at least one group represented by X, Y, and Z is a guanidine group; and
at least one amine group represented by X, Y, or Z is substituted with at least one carboxylate substituent having the formula

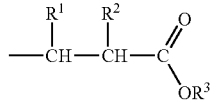

in which:
$R^1$ is a member selected from the group consisting of H, $C_{1-4}$ alkyl, C(O)OH, C(O)O—($C_{1-4}$ alkyl), ($C_{1-4}$ alkylene)-C(O)OH, and ($C_{1-4}$ alkylene)-C(O)O—($C_{1-4}$ alkyl);
$R^2$ is a member selected from the group consisting of H, $C_{1-4}$ alkyl, C(O)OH, C(O)O—($C_{1-4}$ alkyl), ($C_{1-4}$ alkylene)-C(O)OH, and ($C_{1-4}$ alkylene)-C(O)O—($C_{1-4}$ alkyl); and
$R^3$ is a member selected from the group consisting of H and $C_{1-4}$ alkyl.

13. The method of claim 12 wherein m is 1 to 3.

14. The method of claim 12 wherein m is 2 and n is 1 to 10.

15. The method of claim 12 wherein m is 2 and n is 1 to 6.

16. The method of claim 12 wherein m is 2 and n is 4.

17. The method of claim 12 wherein:
m is 2;
n is 1 to 6;
$R^1$ is a member selected from the group consisting of H, $CH_3$, $C(O)OH$, $C(O)OCH_3$, $CH_2C(O)OH$, and $CH_2C(O)OCH_3$;
$R^2$ is a member selected from the group consisting of H, $CH_3$, $C(O)OH$, $C(O)OCH_3$, $CH_2C(O)OH$, and $CH_2C(O)OCH_3$; and
$R^3$ is a member selected from the group consisting of H and $CH_3$.

18. The method of claim 12 wherein said pH gradient extends from about 3.0 to about 13.0.

19. The method of claim 12 wherein said pH gradient extends from about 8.0 to about 13.0.

* * * * *